US012649919B2

(12) United States Patent
Zhao et al.

(10) Patent No.: US 12,649,919 B2
(45) Date of Patent: Jun. 9, 2026

(54) NUCLEIC ACID LIBRARY CONSTRUCTION METHOD AND APPLICATION THEREOF IN ANALYSIS OF ABNORMAL CHROMOSOME STRUCTURE IN PREIMPLANTATION EMBRYO

(71) Applicant: SUZHOU BASECARE MEDICAL DEVICE CO., LTD., Suzhou (CN)

(72) Inventors: Dingding Zhao, Suzhou (CN); Yan Mao, Suzhou (CN); Lingyin Kong, Suzhou (CN); Bo Liang, Suzhou (CN)

(73) Assignee: SUZHOU BASECARE MEDICAL DEVICE CO., LTD, Suzhou (CN)

( * ) Notice: Subject to any disclaimer, the term of this patent is extended or adjusted under 35 U.S.C. 154(b) by 581 days.

(21) Appl. No.: 17/788,590

(22) PCT Filed: Apr. 15, 2021

(86) PCT No.: PCT/CN2021/087503
§ 371 (c)(1),
(2) Date: Jun. 23, 2022

(87) PCT Pub. No.: WO2022/077885
PCT Pub. Date: Apr. 21, 2022

(65) Prior Publication Data
US 2023/0250421 A1      Aug. 10, 2023

(30) Foreign Application Priority Data
Oct. 14, 2020      (CN) ......................... 202011094180.6

(51) Int. Cl.
C12Q 1/6806          (2018.01)
C12N 15/10           (2006.01)
(Continued)

(52) U.S. Cl.
CPC ....... *C12N 15/1093* (2013.01); *C12Q 1/6806* (2013.01); *C12Q 1/6855* (2013.01);
(Continued)

(58) Field of Classification Search
None
See application file for complete search history.

(56) References Cited

U.S. PATENT DOCUMENTS

2003/0190634 A1    10/2003   Barany et al.

FOREIGN PATENT DOCUMENTS

CN          1995384 A        7/2007
CN          102634506 A      8/2012
(Continued)

OTHER PUBLICATIONS

Wang, Junwen et al., "Double restriction-enzyme digestion improves the coverage and accuracy of genome-wide CpG methylation profiling by reduced representation bisulfite sequencing," BMC Genomics, vol. 14, No. 11, Jan. 2013, pp. 1-12.
(Continued)

*Primary Examiner* — Heather Calamita
*Assistant Examiner* — Elizabeth Rose Lafave
(74) *Attorney, Agent, or Firm* — HOWSON & HOWSON, LLP; Kathleen D. Rigaut; Richard F. Kane

(57)            ABSTRACT

Provided are a nucleic acid library construction method and an application thereof in the analysis of an abnormal chromosomal structure of a preimplantation embryo. Enzymatic cleavage is performed by means of combining a first endonuclease and a second endonuclease to capture a DNA sequence within a fixed fragment range. The specific sequences captured are then sequenced. When the average genome sequencing depth is greater than or equal to 3×, an SNP analysis can be performed in the entire range of the genome in order to perform detection of balanced translo-
(Continued)

cation of the embryo and the like by means of a linkage analysis of a family-line sample.

10 Claims, 5 Drawing Sheets

Specification includes a Sequence Listing.

(51) Int. Cl.

| | | |
|---|---|---|
| *C12Q 1/6855* | (2018.01) | |
| *C12Q 1/686* | (2018.01) | |
| *C12Q 1/6869* | (2018.01) | |
| *C12Q 1/6883* | (2018.01) | |
| *C40B 50/06* | (2006.01) | |

(52) U.S. Cl.

CPC ........... *C12Q 1/686* (2013.01); *C12Q 1/6869* (2013.01); *C12Q 1/6883* (2013.01); *C40B 50/06* (2013.01); *C12Q 2600/156* (2013.01)

(56) References Cited

FOREIGN PATENT DOCUMENTS

| | | | |
|---|---|---|---|
| CN | 104232626 | A | 12/2014 |
| CN | 104711362 | A | 6/2015 |
| CN | 105696088 | A | 6/2016 |
| CN | 106566872 | A | 4/2017 |
| CN | 108148830 | A | 6/2018 |
| CN | 109486811 | A | 3/2019 |
| CN | 110283892 | A | 9/2019 |
| CN | 110628891 | A | 12/2019 |
| WO | 01/88189 | A2 | 11/2001 |
| WO | 2016/019360 | A1 | 2/2016 |
| WO | 2018/170659 | A1 | 9/2018 |
| WO | WO-2019113499 | A1 * | 6/2019 ......... C12N 15/1079 |

OTHER PUBLICATIONS

Extended European Search Report, dated Nov. 16, 2023, issued in corresponding European Patent Application No. 21878939.4.

Wei, Shu-Jun et al., "RAD-seq and its application in entomological research", Acta Entomologica Sinica, Scripta Technica, Washington, DC, US, vol. 59, No. 7, Jul. 2016, pp. 767-774.

Bayona-Vasquez, Natalia J. et al., "Adapterama III: Quadruple-indexed, double/triple-enzyme RADseq libraries (2RAD/3RAD)", PeerJ, vol. 7, Oct. 2019, e7724, pp. 1-25.

Ali, Omar A. et al., "RAD Capture (Rapture): Flexible and Efficient Sequence-Based Genotyping," Genetics, vol. 202, No. 2, Feb. 2016, pp. 389-400.

Masset, Heleen et al., "Multi-centre evaluation of a comprehensive preimplantation genetic test through haplotyping-by-sequencing", Human Reproduction vol. 34, No. 8, Jul. 2019, pp. 1608-1619.

* cited by examiner

SEQUENCE LISTING

<160> NUMBER OF SEQ ID NOS: 6

<210> SEQ ID NO 1
<211> LENGTH: 29
<212> TYPE: DNA
<213> ORGANISM: Artificial Sequence
<220> FEATURE:
<223> OTHER INFORMATION: adapter

<400> SEQUENCE: 1
gaacgacatg gctacgatcc gacttcatg                                          29

<210> SEQ ID NO 2
<211> LENGTH: 25
<212> TYPE: DNA
<213> ORGANISM: Artificial Sequence
<220> FEATURE:
<223> OTHER INFORMATION: adapter

<400> SEQUENCE: 2
aagtcggatc gtagccatgt cgttc                                              25

<210> SEQ ID NO 3
<211> LENGTH: 36
<212> TYPE: DNA
<213> ORGANISM: Artificial Sequence
<220> FEATURE:
<223> OTHER INFORMATION: adapter

<400> SEQUENCE: 3
gatcaagtcg gaggccaagc ggtcttagga agacaa                                  36

<210> SEQ ID NO 4
<211> LENGTH: 32
<212> TYPE: DNA
<213> ORGANISM: Artificial Sequence
<220> FEATURE:
<223> OTHER INFORMATION: adapter

<400> SEQUENCE: 4
ttgtcttcct aagaccgctt ggcctccgac tt                                      32

-continued

```
<210> SEQ ID NO 5
<211> LENGTH: 17
<212> TYPE: DNA
<213> ORGANISM: Artificial Sequence
<220> FEATURE:
<223> OTHER INFORMATION: primer

<400> SEQUENCE: 5
gaacgacatg gctacga                                                         17

<210> SEQ ID NO 6
<211> LENGTH: 35
<212> TYPE: DNA
<213> ORGANISM: Artificial Sequence
<220> FEATURE:
<223> OTHER INFORMATION: primer

<400> SEQUENCE: 6
tgtgagccaa ggagttgttg tcttcctaag accgc                                     35
```

NUCLEIC ACID LIBRARY CONSTRUCTION METHOD AND APPLICATION THEREOF IN ANALYSIS OF ABNORMAL CHROMOSOME STRUCTURE IN PREIMPLANTATION EMBRYO

CROSS REFERENCE TO RELATED APPLICATIONS

This application is a § 371 of International Application No. PCT/CN2021/087503, filed Apr. 15, 2021, which claims priority to Chinese Patent Application No. 202011094180.6 filed Oct. 14, 2020, the entire contents of each being incorporated by reference as though set forth in full.

INCORPORATION-BY-REFERENCE OF MATERIAL SUBMITTED IN ELECTRONIC FORM

Incorporated herein by reference in its entirety is the sequence listing submitted via EFS-Web as a text file named SEQLIST.txt, created February 23,2026, and having a size of 1,530 bytes.

TECHNICAL FIELD

The present disclosure relates to the field of molecular biology and, in particular, to a method for constructing nucleic acid libraries and an application thereof to analyses of chromosomal structural rearrangements of preimplantation embryos.

BACKGROUND

Reduced-representation genome sequencing is a method of conducting high-throughput sequencing on specified segments of genomic DNA cleaved by restriction enzymes and obtaining a large number of genetic polymorphism tag sequences to fully demonstrate the whole genome sequencing strategy of a species. The method can reduce the complexity of a genome, simple to implement, reduce a cost, and obtain genetic polymorphism tags in the whole genome without depending on the reference genome. Therefore, the method is widely used in the fields of molecular marker development, genetic map construction, gene/quantitative trait locus (QTL) mapping, a genome-wide association analysis, a population genetic analysis and molecular breeding. However, a small number (generally smaller than 200 thousand) of single-nucleotide polymorphisms (SNPs) can be captured through existing reduced-representation genome sequencing, the process of constructing a library for the existing reduced-representation genome sequencing is relatively complex, tedious library construction processes such as end repair and dA tail addition are required, or fragment sorting needs to be performed through Pippin or glue recycling. Additionally, the library construction method has low compatibility and can be implemented only for a certain sequencing platform and cannot be flexibly compatible with multiple high-throughput sequencing platforms. Therefore, the reduced-representation genome sequencing is rarely applied and popularized in the field of assisted reproduction.

Preimplantation genetic testing (PGT) of embryos refers to a method of analyzing the genetic materials of embryos fertilized in vitro prior to implantation, so as to diagnose whether an embryo is abnormal, screen a healthy embryo for implantation, and prevent the transfer of a genetic disease. At present, the commonly used techniques in the PGT process are fluorescence in situ hybridization (FISH), an SNP array and high-throughput sequencing (next-generation sequencing (NGS)), etc. A detection method based on the high-throughput sequencing is to subject blastomere cells at an eight-cell stage or trophoblastic cells at a blastocyst stage after an embryo fertilized in vitro develops for 3-5 days to single-cell whole genome amplification to obtain genomic DNA, construct sequencing libraries for sequencing, and perform the subsequent analysis according to the sequencing result.

However, to obtain whether an embryo carries a genetic disease, it is generally necessary to design multiple primer pairs for the amplification of SNP loci closely linked upstream and downstream of a gene of the genetic disease when a library is constructed, and a very high volume of data is required to ensure effective SNP loci and the sequencing depth of the SNP loci so that the detection is time-consuming and costly. Moreover, for different genetic diseases, multiple primers for SNP amplification need to be designed separately each time and then multiple primer pairs need to be verified, tested and optimized. Before an embryo is actually detected, a family (including a husband, a wife and a proband) pre-test needs to be performed firstly. Can an embryo sample be detected only when the pre-test result can obtain sufficient effective SNP loci. The whole detection period of this traditional method is too long, and the method has a high risk of failure and is not conducive to clinical application and popularization. Meanwhile, only a small number of SNP loci upstream and downstream of the gene of the genetic disease are captured for sequencing so that an analysis error is easily caused by homologous recombination.

SUMMARY

Based on this, it is necessary to provide a method for constructing nucleic acid libraries, which can reduce the volume of data required for whole genome sequencing and does not require the design of multiple primers for SNPs.

A method for constructing nucleic acid libraries, including the steps below:

acquiring genomic deoxyribonucleic acid (DNA) of a target human-derived sample;

cleaving the genomic DNA using a combination of a first endonuclease and a second endonuclease to obtain high-density digestion products; wherein the combination of the first endonuclease and the second endonuclease can produce an average of 2000-5000 cleavage sites per 1 Mb segment in human genome and produce sticky ends of 2-5 nt at both ends of digestion fragments of the human genome;

ligating the digestion products to sequencing adapters to obtain ligation products; wherein the sequencing adapters comprise a first adapter and a second adapter, the first adapter is capable of being complementary to a sticky end produced after cleavage by the first endonuclease, and the second adapter is capable of being complementary to a sticky end produced after cleavage by the second endonuclease;

screening from the ligation products to obtain fragments of 200 bp to 400 bp;

performing polymerase chain reaction (PCR) amplification using universal primers of high-throughput sequencing platform to obtain sequencing libraries.

In an embodiment, the combination of the first endonuclease and the second endonuclease is MboI and NspI, BfaI and TaqI, or MboI and MspI.

In an embodiment, the first adapter has sequences shown by SEQ ID NO: 1 and SEQ ID NO: 2, and the second adapter has sequences shown by SEQ ID NO: 3 and SEQ ID NO: 4.

In an embodiment, the universal primers of the high-throughput sequencing platform include a forward primer and a reverse primer, where the forward primer is capable of complementary pairing with the first adapter, and the reverse primer is capable of complementary pairing with the second adapter and has a barcode sequence.

In an embodiment, the forward primer has a sequence shown by SEQ ID NO: 5 and the reverse primer has a sequence shown by SEQ ID NO: 6.

In an embodiment, in the cleavage step, the first endonuclease and the second endonuclease have a volume ratio of 1:(0.8-1.2).

In an embodiment, the ligation products are screened through magnetic bead sorting to obtain the fragments of 200 bp to 400 bp.

In an embodiment, the step of acquiring the genomic DNA includes: acquiring cells from an embryo developed to a cleavage stage or a blastocyst stage and performing whole genome amplification of DNA in these cells.

In an embodiment, the method further includes determining concentration of the sequencing libraries.

The present disclosure further provides a method for analyzing chromosomal structural rearrangements of preimplantation embryos based on reduced-representation genome sequencing. The method includes: constructing sequencing libraries of an embryo sample and at least one parent of the embryo sample by the preceding method for constructing nucleic acid libraries, then performing sequencing, and analyzing a chromosome of the embryo sample according to the sequencing result.

In an embodiment, the analysis step specifically includes: analyzing chromosomal structural variations and analyzing chromosomal aneuploidy variations.

In the method for constructing nucleic acid libraries of the present disclosure, the whole genome is digested with the combination of the first endonuclease and the second endonuclease, where the combination of the first endonuclease and the second endonuclease can produce an average of 2000-5000 cleavage sites per 1 Mb segment in the human genome, the cleavage sites are uniformly distributed and cover more than 95% of genome windows, digestion fragments are mainly distributed at 100 bp to 600 bp, and sticky ends of 2-5 nt are produced at both ends of the digestion fragments. Unlike random digestion, the combination of the first endonuclease and the second endonuclease is used herein to digest only particular regions (10% to 20%) of the whole genome, for the purpose of targeted capture rather than fragmentation only, and then captured fragments with desired sizes are obtained through screening for sequencing, achieving a higher sequencing depth and more effective information with the same volume of data. Using the method for constructing nucleic acid libraries of the present disclosure, 900,000 or more SNP loci and 150,000 or more indels (insertion and deletion markers) can be obtained through next-generation sequencing with a small volume (20 M, 40 M or 80 M) of data, where 500,000 or more SNP loci have a sequencing depth of higher than 10×. In the present disclosure, based on the reduced-representation genome sequencing, an advantageous endonuclease combination is screened out to obtain sufficient effective SNP loci for whole genome genotyping, the library construction process is simplified using particular sequencing adapters and a magnetic bead sorting strategy, and a technical system for performing a preimplantation genetic analysis on captured SNPs of embryos without designing multiple primers is established, which reduces the volume of data required for whole genome sequencing and can simultaneously analyze the chromosomal structural rearrangements and the chromosomal aneuploidy in one experiment.

DETAILED DESCRIPTION

Figure 1:
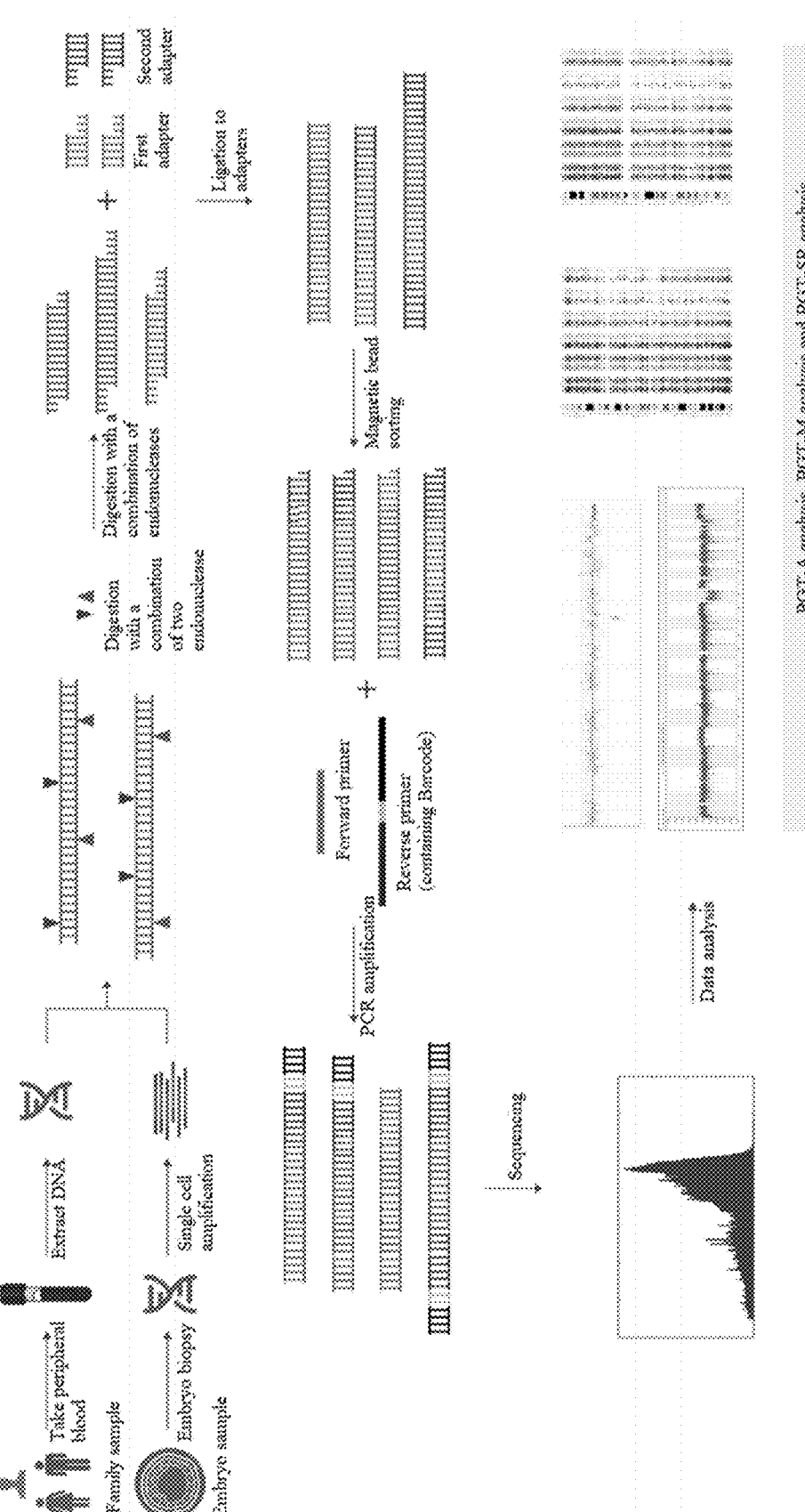
FIG. 1 is a schematic diagram showing the principle of a method for constructing nucleic acid libraries according to an embodiment of the present disclosure.

For a better understanding of the present disclosure, the present disclosure is described below in more detail and preferred embodiments of the present disclosure are provided. However, the present disclosure may be implemented in many different forms and is not limited to the embodiments described herein. Rather, these embodiments are provided for a more through and comprehensive understanding of the content disclosed in the present disclosure.

Unless otherwise defined, all technical and scientific terms used herein have meanings the same as those commonly understood by those skilled in the art to which the present disclosure pertains. Terms used in the specification of the present disclosure are only used for describing embodiments and not intended to limit the present disclosure. The term "and/or" used herein includes any or all combinations of one or more listed associated items.

Explanation of Terms

Chromosomes are the basic substances constituting a nucleus and the carriers of genes. Chromosomal structural rearrangements refer to chromosome aberrations and chromatid aberrations due to a breakage-rechange or exchange mechanism of chromosomes or chromatids. Chromosome translocations are the most common chromosomal structural rearrangements and mainly refer to the exchange of chromosomal fragments between non-homologous chromosomes.

Balanced translocation refers to that two non-homologous chromosomes are broken and mis-spliced to form two structurally rearranged chromosomes and includes reciprocal translocation and Robertsonian translocation. Since the original total number of genes is retained during a balanced translocation of chromosomes, an individual carrying the balance translocation has no obvious disease phenotype but often has a reproductive disorder. This is mainly because the carrier of the balanced translocation may produce unbalanced gametes during meiosis, resulting in a decrease or an increase of a certain genetic material, destroying the balance of genetic materials, and eventually causing fetal malformation or infertility. Theoretically, a carrier of a balanced translocation of two chromosomes can form a tetrad during meiosis. According to different separation manners, various types of gametes can be produced. It is generally believed that at least 18 types of different gametes can be produced through 2:2 separation and 1:3 separation, and 10 types of gametes can be produced through 4:0 separation. Researches show that the probability of 4:0 separation is relatively small, and the common separation manner is 2:2 separation. Of six types of gametes produced by a carrier of a Robertsonian translocation of non-homologous chromosomes, 1/6 are normal gametes, 1/6 carries the translocation, and 4/6 are abnormal gametes. When a patient suffering from a balanced translocation is fertile with a normal person, chromosomal euploidy, monosomy or trisomy due to an unbalanced translocation, or a carrier of a balanced translocation will occur in an embryo depending on the type of gamete separation. Chromosomal aneuploidy is the leading cause of unexplained abortions, fetal malformations, infertility and stillbirths.

FISH is a method for hybridizing nucleic acid sequences of to-be-tested samples in situ with fluorescence-labeled probes and analyzing the structures and number of chromosomes for DNA by a fluorescence microscope. After particular chromosomes in embryonic cells are hybridized with FISH probes, the detected chromosomes may be observed under the fluorescence microscope to determine whether a translocation and a copy number variation (CNV) are occurred. The FISH has the advantages of rapidity and sensitivity. However, the FISH has a limitation of a low throughput. Since the fluorescence signals of only five different chromosome probes can be observed at the same time with the fluorescence microscope currently, two or more rounds of hybridization are required to analyze more chromosomes. However, multiple rounds of hybridization of single cells increase an error rate. Thus, the FISH can only detect a limited number of chromosomes and cannot detect the aneuploidy of all chromosomes.

A SNP array is a high-density microarray chip containing a large number of SNP loci. Most SNP chips can detect more than 600,000 SNPs. Not only a copy number variation of the whole chromosome can be detected through an analysis of a signal intensity ratio of heterozygous alleles, but also an embryo carrying a balanced translocation can be distinguished from a normal embryo through a SNP linkage analysis within the whole genome of a family. Detection techniques based on the SNP array have been successfully used for distinguishing the normal embryo from the embryo carrying the balanced translocation. However, the technique uses probes with immobilized and known variations and has relatively poor changeability and flexibility, a few post-hybridization loci exist in some complex regions, and background interference after hybridization results in a risk of a typing failure. For the detection of embryo samples, the CNV is detected with low sensitivity in that the CNV cannot be detected when the volume of data is less than 10 M, and a chimera is detected with a poor effect.

A single-nucleotide polymorphism (SNP) mainly refers to the polymorphism of a DNA sequence due to the variation of a single nucleotide at a genome level. A haplotype refers to a combination of single-nucleotide polymorphisms in a particular region of a chromosome, which are correlated to each other and tend to be inherited as a whole to an offspring. For a sequencing depth, for example, in an embodiment, a sequencing depth of 1000× represents that a specific PCR amplification product is subjected to sequencing 1000 times.

PGT-SR is targeted at the detection of whether embryonic chromosomes have inversions, balanced translocation and Robertsonian translocations and is equivalent to part of original preimplantation genetic diagnosis (PGD). SR refers to "chromosomal structural rearrangements". PGT-A is a technique for detecting the presence of aneuploidy in embryonic chromosomes and is equivalent to original preimplantation genetic screening (PGS). A refers to "aneuploidy". PGT-M is targeted at the detection of whether an embryo carries some mutated genes that can cause monogenic diseases and is equivalent to part of the original PGD. M refers to "monogenic/single gene defects".

According to an embodiment of the present disclosure, a method for constructing nucleic acid libraries includes steps S1 to S5 described below.

In S1, genomic DNA of a target human-derived sample is acquired.

In S2, the genomic DNA is cleaved using a combination of a first endonuclease and a second endonuclease to obtain high-density digestion products. The combination of the first endonuclease and the second endonuclease may produce an average of 2000-5000 cleavage sites per 1 Mb segment in human genome and produce sticky ends of 2-5 nt at both ends of digestion fragments of the human genome.

In S3, the digestion products are ligated to sequencing adapters to obtain ligation products. The sequencing adapters include a first adapter and a second adapter, the first adapter can be complementary to a sticky end produced after cleavage by the first endonuclease, and the second adapter can be complementary to a sticky end produced after cleavage by the second endonuclease through cleavage.

In S4, the ligation products are screened to obtain fragments of 200 bp to 400 bp.

In S5, PCR amplification is performed using universal primers of a high-throughput sequencing platform to obtain sequencing libraries.

In the method for constructing nucleic acid libraries of the present disclosure, the whole genome is digested with the combination of the first endonuclease and the second endonuclease, where the combination of the first endonuclease and the second endonuclease can produce an average of 2000-5000 cleavage sites per 1 Mb segment in the human genome, the cleavage sites are uniformly distributed and cover more than 95% of genome windows, digestion fragments are mainly distributed at 100 bp to 600 bp, and sticky ends of 2-5 nt are produced at both ends of the digestion fragments. Unlike random digestion, the combination of the first endonuclease and the second endonuclease is used herein to digest only particular regions (10% to 20%) of the whole genome, for the purpose of targeted capture rather than fragmentation only, and then captured fragments with desired sizes are obtained through screening for sequencing, achieving a higher sequencing depth and more effective information with the same volume of data. Using the method for constructing nucleic acid libraries of the present disclosure, 900,000 or more SNP loci and 150,000 or more indels (insertion and deletion markers) can be obtained through next-generation sequencing with a small volume (20 M, 40

M or 80 M) of data, where 500,000 or more SNP loci have a sequencing depth of higher than 10×.

Therefore, a SNP analysis can be performed within a range of the whole genome by the method for constructing nucleic acid libraries of the present disclosure when an average sequencing depth of the genome is higher than 3× so that balanced translocations and the like of embryos are detected through a linkage analysis of family samples. The method reduces a volume of data required for whole genome sequencing, ensures effective SNP loci and their depths, and increases the number of SNP loci available for haplotypes so that sufficient SNPs and indels covering the whole genome and capable of being used for analyzing haplotypes are obtained with a very small volume of sequencing data, and multiple PCR primers do not need to be designed for SNPs, greatly reducing the volume of data required and a detection cost. Meanwhile, the ability to detect CNV and chimera is significantly increased, and the CNV above 5 M can be detected and more than 30% of chimeras can be detected.

In a specific example, the combination of the first endonuclease and the second endonuclease is, but not limited to, MboI and NspI, BfaI and TaqI, or MboI and MspI.

In a specific example, as shown in Table 1, the first adapter has sequences shown by SEQ ID NO: 1 and SEQ ID NO: 2, and the second adapter has sequences shown by SEQ ID NO: 3 and SEQ ID NO: 4. These adapters are formed by adding sticky ends CATG and GATC to two adapters from BGI sequencing platform, respectively, so that they can be complementary to the sticky ends produced after digestion with NspI and MboI. It is to be understood that original adapter sequences for modification include, but are not limited to, adapter sequences applicable to Thermo Fisher Scientific, Illumina, BGI and other sequencing platforms, and the sequences of the added sticky ends may be adjusted according to different endonucleases.

TABLE 1

| Adapter sequence | |
| --- | --- |
| Sequencing Adapter | Sequence |
| First adapter | 5'-GAACGACATGGCTACGATCCGA CTT*CATG*-3' (SEQ ID NO: 1)<br>5'-AAGTCGGATCGTAGCCATGTCG TTC-3' (SEQ ID NO: 2) |
| Second adapter | 5'-*GATC*AAGTCGGAGGCCAAGCGG TCTTAGGAAGACAA-3' (SEQ ID NO: 3)<br>5'-TTGTCTTCCTAAGACCGCTTGG CCTCCGACTT-3' (SEQ ID NO: 4) |

In a specific example, the universal primers of the high-throughput sequencing platform include a forward primer and a reverse primer, where the forward primer is capable of complementary pairing with the first adapter, and the reverse primer is capable of complementary pairing with the second adapter and has a barcode sequence. In this manner, particular barcode information can be introduced during the PCR amplification of the libraries. When to-be-tested DNA molecules are from multiple test samples, each sample may be labeled with a different tag sequence (barcode) to differentiate the samples during sequencing so that the sequencing is performed simultaneously on multiple samples.

In a specific example, as shown in Table 2, the forward primer has a sequence shown by SEQ ID NO: 5 and the reverse primer has a sequence shown by SEQ ID NO: 6.

They are universal primers for the preceding two adapters from BGI sequencing platform (DNBSEQ™). It is to be understood that when different sequencing adapters are used, the sequences of the universal primers may be adjusted as required.

TABLE 2

| Primer sequences | |
| --- | --- |
| Universal Primer | Sequence |
| Forward primer | 5'-GAACGACATGGCTACGA-3' (SEQ ID NO: 5) |
| Reverse primer | 5'-TGTGAGCCAAGGAGTTG(barcode)TTGTCTTCC TAAGACCGC-3' (SEQ ID NO: 6) |

Optionally, in the cleavage step, the first endonuclease and the second endonuclease have a volume ratio of 1:(0.8-1.2).

In a specific example, the ligation products are screened through magnetic bead sorting to obtain the fragments of 200 bp to 400 bp. Preferably, the magnetic beads are AMPure XP™ magnetic beads.

In a specific example, the step of acquiring the genomic DNA includes: acquiring cells from an embryo developed to a cleavage stage or a blastocyst stage and performing whole genome amplification of DNA in these cells.

In a specific example, the method for constructing nucleic acid libraries further includes determining concentration of the sequencing libraries.

According to an embodiment of the present disclosure, a method for analyzing chromosomal structural rearrangements of preimplantation embryos based on reduced-representation genome sequencing includes: constructing sequencing libraries of an embryo sample and at least one parent (such as a father sample and a mother sample) of the embryo sample by the preceding method for constructing nucleic acid libraries, then performing sequencing, and analyzing a chromosome of the embryo sample according to the sequencing result.

It is to be understood that the detection object of the detection method is an embryo to be implanted into a uterus rather than a living human body or animal body, and the detection result does not involve a disease diagnosis result of both parents, so the detection method does not belong to a disease diagnosis and treatment method. Additionally, the method may also be used for a non-disease diagnosis and treatment purpose such as the detection of a dead embryo sample.

Optionally, the samples of both parents are selected from one or more of peripheral blood genomic DNA, semen DNA, oral mucosal cell DNA and a whole genome amplification product of cells. Preferably, the amount of DNA in each sample is greater than 500 ng.

In a specific example, the analysis step specifically includes: analyzing chromosomal structural variations, analyzing chromosomal aneuploidy variations, analyzing single gene genetic diseases and/or analyzing copy number variations.

In a specific example, for a family with a familial/hereditary balanced translocation, the preceding method for constructing nucleic acid libraries is used for constructing sequencing libraries for a couple having a balanced translocation carrier, at least one relative of the translocation carrier and an embryo generated by the couple, then sequencing is performed, and a SNP analysis is performed on whole genome sequences obtained after sequencing. SNP loci which are heterozygous in the translocation carrier of the couple, are homozygous in the other partner, and are homozygous in the relative of the translocation carrier are selected as effective SNP loci. These effective SNP loci of all samples are analyzed, and haplotype maps of all the samples are constructed, so as to determine an abnormal chromatid of the translocation carrier. The region where the balanced translocation breakpoint is located is positioned, and whether the embryo carries the abnormal chromatid is determined according to haplotype within a range of 1 M to 5 M upstream and downstream of the breakpoint so that whether the embryo carries the balanced translocation is determined.

A whole genome CNV analysis may also be performed on sequencing data. The analysis method is as follows: base sequences obtained through DNA sequencing after single cell amplification are compared with a standard sequence hg19 of the human genome using BWA software, and an exact position of each base sequence obtained through sequencing on a chromosome is determined. A low-quality base sequence, a base sequence matched to multiple chromosomes and a base sequence not exactly matched to a chromosome are removed, ensuring the accuracy of the sequencing data and the uniqueness of the position of each base sequence. The whole chromosome is divided into non-overlapping regions each having a size of 100 kb, and the number of unique matching sequences obtained in each window of 100 kb is calculated. A GC content deviation is corrected, windows are merged, and window data is homogenized. The window data is compared with reference data, log 2RR is calculated, the breakpoint is calculated through CBS, the copy number is calculated, and the final result is generated through annotation.

In a specific example, for a family newly found carrying a balanced translocation, the preceding method for constructing nucleic acid libraries is used for constructing sequencing libraries for a couple having a balanced translocation carrier and an embryo generated by the couple, and then sequencing is performed. The whole genome CNV analysis is performed on the embryo by the analysis method as described above. Embryo E1 having a copy number variation of a chromosome due to the balanced translocation is selected, and then the SNP analysis is performed on whole genome sequences obtained through sequencing. SNP loci which are heterozygous in the translocation carrier of the couple and are homozygous in the other partner are selected as effective SNP loci. These effective SNP loci of all samples are analyzed, and haplotype maps of all the samples are constructed. According to separation law, Embryo E1 inherits an abnormal chromatid from a parent with certainly so that the abnormal chromatid of the translocation carrier is determined. The region where a balanced translocation breakpoint is located is positioned, and whether another embryo carries the abnormal chromatid is determined according to haplotype within a range of 1 M to 5 M upstream and downstream of the breakpoint so that whether the embryo carries the balanced translocation is determined.

The method for analyzing chromosomes of preimplantation embryos in the present disclosure can obtain sufficient SNP loci and indel loci in the whole genome without designing multiple PCR primers for different diseases and can implement the aneuploidy screening of 23 pairs of chromosomes simultaneously. Moreover, the coverage of the whole chromosome where a target gene is located can reduce an effect of homologous recombination on the analysis. The chromosomal structural rearrangements of embryos are effectively analyzed through a family analysis at a high success rate, which is applicable to normal embryos and carrier embryos in the determined families with Robertsonian translocations and reciprocal translocations.

Specific examples are described below.

Example 1 Detection of Embryos in a Family with a Hereditary Balanced Translocation One family having a chromosomal balanced translocation carrier was recruited (results from chip assay have been confirmed), where the family had received assisted reproduction. Information about the family is shown in Table 3. The peripheral blood samples (three blood samples in total) of the balanced translocation carrier, his wife and a parent from which the balanced translocation of the carrier is inherited (5 mL for each blood sample) were collected and stored in an EDTA anticoagulant blood collection tube. At the same time, the whole genome amplification products of 5 embryo biopsy samples of the couple were obtained. Genomic DNA of the family was extracted by a whole blood extraction kit. The analysis of the chromosomal balanced translocation before embryo implantation was performed by the method of the present disclosure.

TABLE 3

| Karyotypes of the family with the balanced translocation (chip results) | | |
| --- | --- | --- |
| No. | Family | Karyotype |
| 1 | Wife | 46, XX |
| 2 | Husband | 46, XY, t(8; 14)(p23; q24)mat |
| 3 | Mother of the husband | 46, XX, t(8; 14)(p23; q24) |
| 5481101E | Embryo 1 | Euploid |
| 5481102E | Embryo 2 | Euploid |
| 5481103E | Embryo 3 | Euploid |
| 5481104E | Embryo 4 | del(8)(p23.3p23.1); dup(14)(q23.2q32.33) |
| 5481105E | Embryo 5 | del(8)(p23.3p23.1); dup(14)(q23.2q32.33) |

Figure 2:
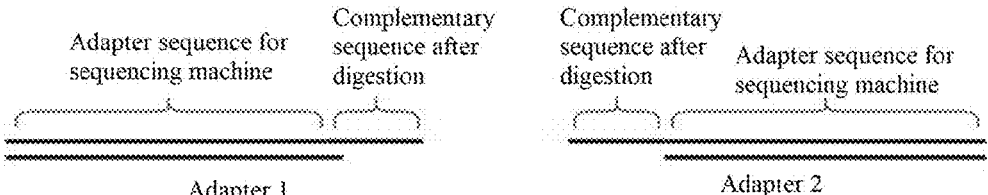
FIG. 2 is a structural diagram of sequencing adapters according to an embodiment of the present disclosure.
Figure 3:
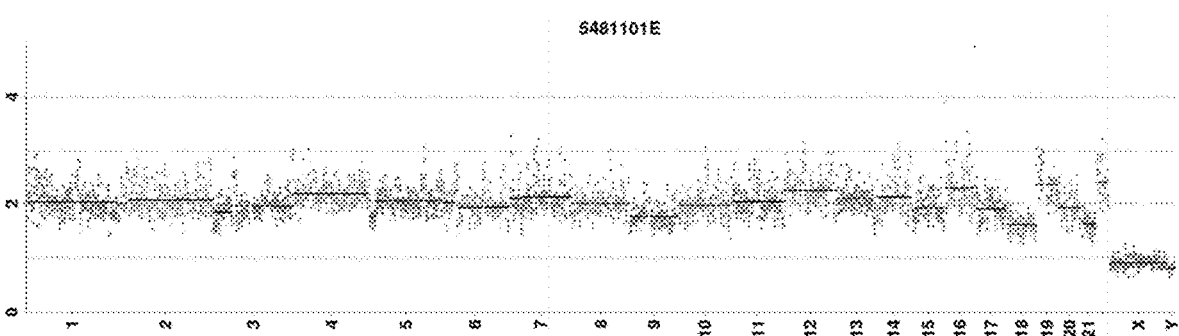
FIG. 3 is a scatter plot of the detection results of 5481101E embryo (euploidy) in Example 1.
Figure 4:
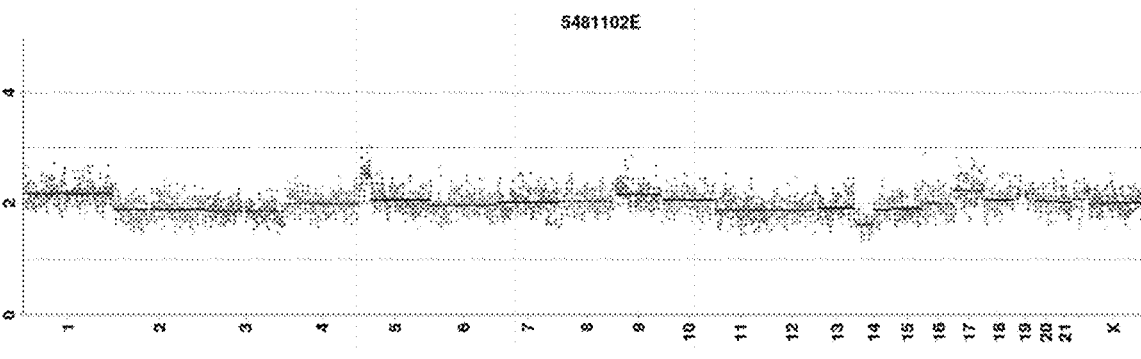
FIG. 4 is a scatter plot of the detection results of 5481102E embryo (euploidy) in Example 1.
Figure 5:
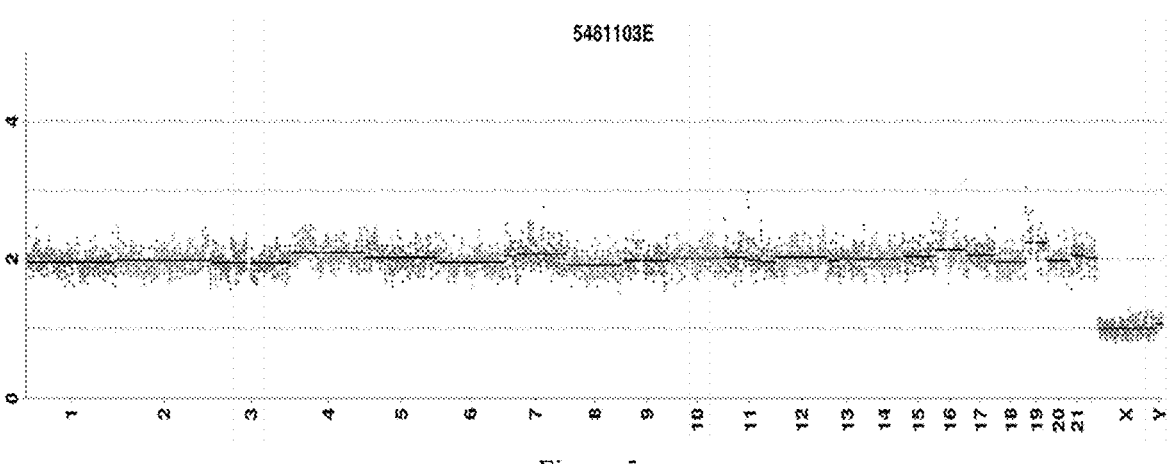
FIG. 5 is a scatter plot of the detection results of 5481103E embryo (euploidy) in Example 1.
Figure 6:
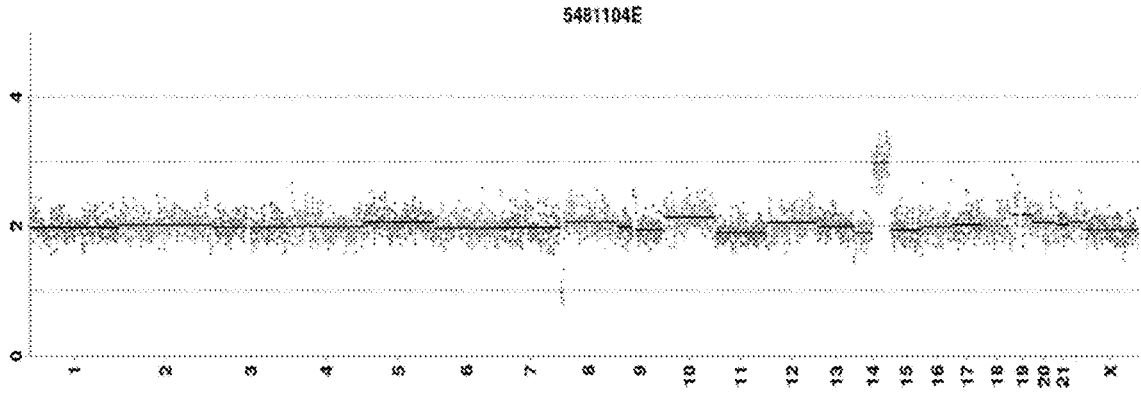
FIG. 6 is a scatter plot of the detection results of 5481104E embryo (del(8)(p23.3p23.1);dup(14)(q23.2q32.33)) in Example 1.
Figure 7:
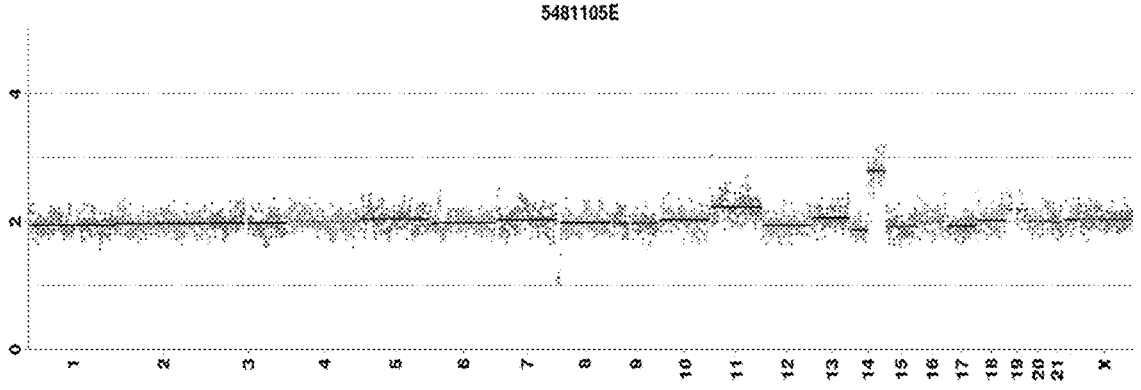
FIG. 7 is a scatter plot of the detection results of 5481105E embryo (del(8)(p23.3p23.1);dup(14)(q23.2q32.33)) in Example 1.

The principle is shown in FIG. 1. Particular cleavage sites on the genome were identified by a combination of endonucleases and the genomic DNA was cleaved so that the genomic DNA was broken into fixed sequence fragments, and sticky ends retained after endonuclease cleavage were formed at two ends of the broken fragments. Two sequencing adapters capable of being complementary to the sticky ends produced after endonuclease cleavage were designed, the adapters were ligated to the broken genome sequences, and PCR amplification was performed to form sequencing libraries. Fragments with particular lengths were enriched from the constructed sequencing libraries and then subjected to sequencing, where each sample required ≥8 Gb of sequencing data. The structures of the sequencing adapters are shown in FIG. 2, each of which includes a sequence complementary to a sticky end of a digestion fragment and an original sequencing adapter sequence for various sequencing platforms.

1. Digestion

Embryo samples were subjected to whole genome amplification using a whole genome amplification kit, QIAGEN® REPLI-g Single Cell Kit or TaKaRa™ PicoPLEX Single Cell WGA kit. 500 ng of DNA was prepared and added with water to 17 μL. A mixed digestion solution Mix1 was prepared according to Table 4. The mixed digestion solution Mix1 (3 μL) was added to the sample, blown uniformly with a gun, and briefly centrifuged.

TABLE 4

Mixed digestion solution

| Components of the Mixed Digestion Solution Mix1 | Volume (μL) |
| --- | --- |
| Endonuclease reaction buffer solution | 2 μL |
| Endonuclease 1, NspI | 0.5 μL |
| Endonuclease 2, MboI | 0.5 μL |
| Total volume | 3 μL |

The centrifuged DNA was placed into a PCR machine. The setup procedures of the PCR machine are shown in Table 5.

TABLE 5

PCR procedures

| Step | Temperature | Time |
| --- | --- | --- |
| 1 | 37° C. | 15 min |
| 2 | 65° C. | 20 min |
| 3 | 4° C. | Hold |

2. Ligation to Adapters

Two adapters from BGI sequencing platform (DNB-SEQ™) were used in this example:

```
adapter 1:
5'-GAACGACATGGCTACGATCCGACTTCATG-3'
and

5'-AAGTCGGATCGTAGCCATGTCGTTC-3';

adapter 2:
5'-GATCAAGTCGGAGGCCAAGCGGTCTTAGGAAGACAA-3'
and

5'-TTGTCTTCCTAAGACCGCTTGGCCTCCGACTT-3'.
```

A mixed adapter solution Mix2 was prepared according to Table 6. The mixed adapter solution Mix2 (5 μL) was added to the digested DNA, blown uniformly with a gun, and briefly centrifuged.

TABLE 6

Mixed adapter solution

| Components of the Mixed Adapter Solution Mix2 | Volume |
| --- | --- |
| Adapter 1 | 2.5 μL |
| Adapter 2 | 2.5 μL |
| Total volume | 5 μL |

The centrifuged DNA was placed into the PCR machine. The setup procedures of the PCR machine are shown in Table 7.

TABLE 7

PCR procedures

| Step | Temperature | Time |
| --- | --- | --- |
| 1 | 65° C. | 10 min |
| 2 | 4° C. | Hold |

A mixed ligase solution Mix3 was prepared according to Table 8. The mixed ligase solution Mix3 (5 μL) was added to the preceding DNA and adapters, blown uniformly with a gun (without being vortexed), and briefly centrifuged.

TABLE 8

Mixed ligase solution

| Mixed Ligase Solution Mix3 | Volume |
| --- | --- |
| Ligase buffer solution | 3 μL |
| DNA ligase | 2 μL |
| Total volume | 5 μL |

The centrifuged DNA was placed into the PCR machine. The setup procedures of the PCR machine are shown in Table 9.

TABLE 9

PCR procedures

| Step | Temperature | Time |
| --- | --- | --- |
| 1 | 22° C. | 15 min |
| 2 | 65° C. | 10 min |
| 3 | 4° C. | Hold |

3. Fragment Screening

Water was added to 100 μL, and AMPure XP™ magnetic beads (60 μL) were added, blown uniformly with a gun, placed still for 5 min at room temperature, and placed on a magnet. When the liquid was clear, the supernatant was transferred to a new EP tube, added with AMPure XP™ magnetic beads (20 μL), placed still for 5 min at room temperature, and placed on a magnet. When the liquid was clear, the supernatant was removed, washed with 200 μL of 80% alcohol, dried at room temperature, and eluted with 22 μL of low TE.

4. Concentration Determination

The sample (2 μL) was aspirated for Qubit concentration determination.

5. PCR Amplification

The fragments screened out (10 ng) were subjected to PCT amplification to obtain libraries. A mixed PCR reaction solution Mix4 was prepared according to Table 10.

```
PCR primer:
F: 5'-GAACGACATGGCTACGA-3'

R: 5'-TGTGAGCCAAGGAGTTG(barcode)TTGTCTTC

CTAAGACCGC-3'
```

13

TABLE 10

| Mixed PCR reaction solution | |
| --- | --- |
| Component | Volume |
| PCR amplification enzyme | 25 μL |
| Universal Primer | 1.25 μL |
| Nuclease-free water | 2.5 μL |
| Total volume | 28.75 μL |

The sample after fragment screening (20 μL) was put into a PCR tube, added with the mixed PCR reaction solution Mix4 (28.75 μL) and barcode-containing specific primers (1.25 μL), and briefly centrifuged. The mixture was put into the PCR machine. The setup procedures are shown in Table 11.

TABLE 11

| PCR procedures | | |
| --- | --- | --- |
| Temperature | Time | Cycle |
| 98° C. | 45 s | 1 |
| 98° C. | 15 s | 7 |
| 60° C. | 30 s | |
| 72° C. | 55 s | |
| 4° C. | Hold | 1 |

6. Library Purification

After the reaction was completed, the system was briefly centrifuged, added with AMPure XP™ magnetic beads (50 μL), blown uniformly with a gun, placed still for 5 min at room temperature, and placed on the magnet. When the liquid was clear, the supernatant was removed and washed with 200 μL of 80% alcohol. The preceding was repeated once. The magnetic beads were dried at room temperature and resuspended with 40 μL of low TE, and the DNA was eluted.

7. Concentration Determination

The sample (2 μL) was aspirated for concentration determination using a Qubit® fluorometer.

8. Sequencing

A platform was selected according to the type of the adapters for next-generation sequencing. In this example, BGI sequencing platform was used for sequencing.

9. Data Analysis

The sequencing data obtained through sequencing was analyzed and compared with a reference genome. SNP loci were obtained from the data through variation identification, and whether the chromosome of the embryo was abnormal in structure was determined by constructing a genetic map, so as to distinguish an embryo carrying the balanced translocation or a normal embryo.

10. Detection Performance

A deletion greater than or equal to 5M can be detected, and embryonic inheritance in a family with determined balanced translocation (Robertsonian translocation and reciprocal translocation) can be detected.

11. Detection Results

Figures 8, 9:
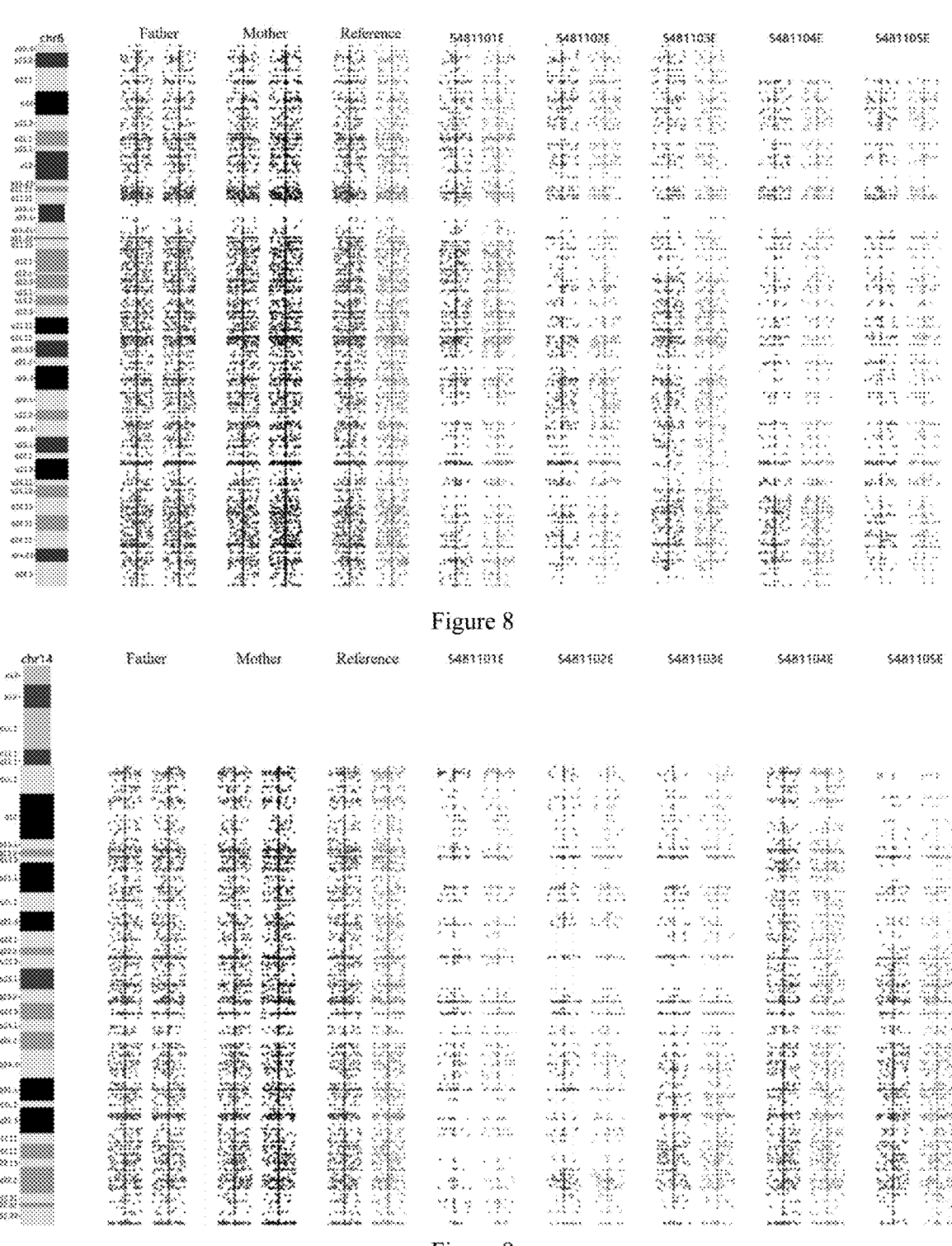
FIG. 8 shows the analysis results of a balanced translocation on chromosome 8 of each embryo in Example 1.
FIG. 9 shows the analysis results of a balanced translocation on chromosome 14 of each embryo in Example 1.

The PGT-A detection results of the five embryo samples are shown in FIGS. 3 to 7. The analysis results of the balanced translocation on chromosome 8 of each embryo are shown in FIG. 8. With the mother of the husband as a reference sample, the haplotype analyses in the map are the husband, the wife, the reference sample (the mother of the husband), 5481101E embryo, 5481102E embryo, 5481103E embryo, 5481104E embryo and 5481105E embryo in sequence from left to right. The analysis results of the balanced translocation on chromosome 14 of each embryo are shown in FIG. 9. With the mother of the husband as the reference sample, the haplotype analyses in the map are the husband, the wife, the reference sample (the mother of the husband), 5481101E embryo, 5481102E embryo, 5481103E embryo, 5481104E embryo and 5481105E embryo in sequence from left to right.

Since the husband among the subjects of the detection is the translocation carrier and the chromosomes related to the translocation are chromosome 8 and chromosome 14, that is, the husband includes one normal chromatid 8, one normal chromatid 14 and two translocated chromatids (8p23 and 14q24 translocations), according to the detection results of the mother of the husband, it is presumed that the husband inherits two translocated chromatids from the mother and inherits one normal chromatid 8 and one normal chromatid 14 from the father. Therefore, the colors of chromatid 8 and chromatid 14 of the mother, which are the same as those of the husband, are abnormal (blue), while the color of another chromatid of the husband is normal (red). In conjunction with the detection results of the copy number variations of the chromosomes of the embryos, it can be seen that 5481101E embryo is a balanced translocation carrier; 5481102E embryo is a balanced translocation carrier; 5481103E embryo is a balanced translocation carrier; 5481104E embryo has copy number variations on chromosome 8 and chromosome 14 and thus is an unbalanced translocation carrier; and 5481105E embryo has copy number variations on chromosome 8 and chromosome 14 and thus is an unbalanced translocation carrier.

Example 2

Samples of a cell line with chromosomal aneuploidy (5 cells) were subjected to whole genome amplification by an MDA method, where the details are shown in Table 12.

TABLE 12

| Details of the cell line samples | | |
| --- | --- | --- |
| No. | Gender | Karyotype |
| GM10932 | Male | 46, XY, del(8)(p23p23).arr8p23.1(7237777-12457161) × 1 |

Figure 10:
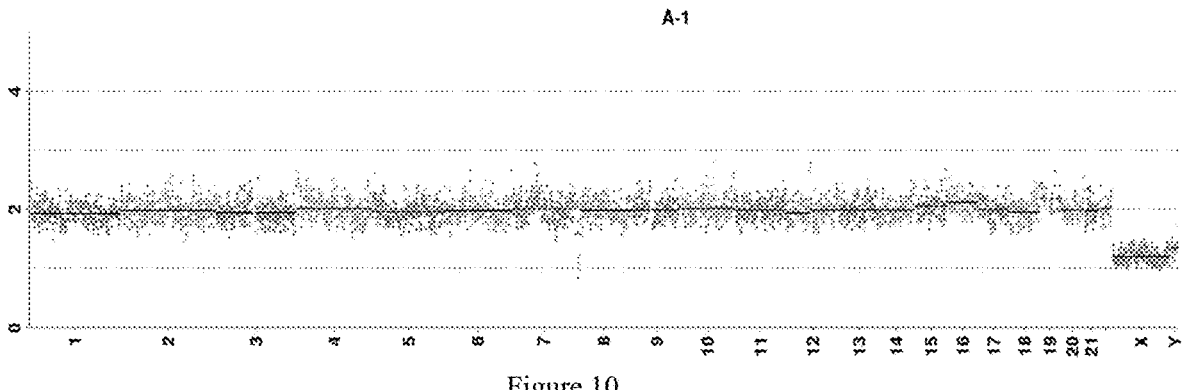
FIG. 10 is a scatter plot of the detection results of a cell line (del(8)-5.2M) in Example 2.

The samples were detected by the method of Example 1. The PGT-A data analysis results of the cell line are shown in FIG. 10. The detection results show that the method can detect a deletion greater than 5M.

Comparative Example 1

In Comparative Example 1, the embryo samples in Example 1 were detected using a SNP-array chip (Karyo-mapping gene chip).

The valid data of chromosomes in Example 1 and Comparative Example 1 was compared. Using 5481105E embryo as an example, the effective loci of the chromosomes are compared in Table 13. Table 13 shows that the data on effective loci (embryo samples) in Example 1 is more than the data of the chip.

TABLE 13

Comparison of effective loci of the chromosomes of embryos in Example 1 with those of the chip

| Chr | Present Disclosure | | | | | | SNP-Array Chip | | | | | |
|-----|------|------|------|------|------|------|------|------|------|------|------|------|
|     | Ref | 01E | 02E | 03E | 04E | 05E | Ref | 01E | 02E | 03E | 04E | 05E |
| chr1 | 3401 | 1706 | 2003 | 1130 | 1402 | 1233 | 2270 | 1386 | 1375 | 807 | 1367 | 1074 |
| chr10 | 2298 | 696 | 634 | 1270 | 1170 | 503 | 1502 | 519 | 435 | 977 | 1017 | 338 |
| chr11 | 2217 | 636 | 767 | 788 | 1123 | 619 | 1487 | 434 | 555 | 553 | 941 | 372 |
| chr12 | 2077 | 882 | 544 | 735 | 777 | 875 | 1457 | 647 | 409 | 586 | 648 | 761 |
| chr13 | 1696 | 839 | 744 | 747 | 519 | 745 | 1112 | 595 | 450 | 563 | 493 | 667 |
| chr14 | 1440 | 394 | 400 | 513 | 954 | 737 | 951 | 273 | 263 | 384 | 664 | 522 |
| chr15 | 1322 | 634 | 765 | 783 | 417 | 586 | 1008 | 579 | 662 | 698 | 386 | 535 |
| cor16 | 1048 | 576 | 264 | 268 | 384 | 249 | 802 | 455 | 236 | 243 | 393 | 278 |
| chr17 | 1227 | 341 | 377 | 511 | 287 | 600 | 1015 | 236 | 199 | 442 | 229 | 716 |
| chr18 | 1274 | 335 | 683 | 603 | 356 | 399 | 992 | 301 | 611 | 602 | 220 | 284 |
| chr19 | 845 | 257 | 183 | 191 | 278 | 494 | 772 | 220 | 142 | 153 | 321 | 588 |
| chr2 | 3884 | 1241 | 1576 | 1778 | 1531 | 1697 | 2464 | 757 | 1084 | 1311 | 1348 | 1390 |
| chr20 | 945 | 220 | 241 | 227 | 423 | 544 | 843 | 184 | 193 | 187 | 458 | 598 |
| chr21 | 615 | 118 | 388 | 132 | 166 | 169 | 465 | 91 | 325 | 90 | 173 | 163 |
| chr22 | 487 | 331 | 149 | 240 | 208 | 92 | 534 | 299 | 218 | 313 | 337 | 126 |
| chr3 | 3438 | 948 | 800 | 807 | 1804 | 1710 | 2210 | 565 | 397 | 476 | 1567 | 1324 |
| chr4 | 3655 | 734 | 1603 | 1870 | 1218 | 1923 | 2112 | 429 | 948 | 1328 | 1012 | 1467 |
| chr5 | 3252 | 1317 | 1570 | 1592 | 666 | 619 | 1882 | 762 | 925 | 1136 | 521 | 393 |
| chr6 | 3413 | 1867 | 1838 | 987 | 1569 | 1646 | 2374 | 1378 | 1380 | 864 | 1413 | 1388 |
| chr7 | 2878 | 1631 | 764 | 1569 | 1132 | 909 | 1627 | 1064 | 410 | 1063 | 834 | 596 |
| chr8 | 2073 | 996 | 803 | 916 | 655 | 580 | 864 | 450 | 281 | 455 | 364 | 235 |
| chr9 | 1842 | 512 | 536 | 487 | 601 | 1053 | 806 | 208 | 148 | 176 | 267 | 586 |
| total | 45327 | 17211 | 17632 | 18044 | 17638 | 17982 | 29549 | 11832 | 11646 | 13407 | 15073 | 14401 |

Example 3

The method in this example is basically the same as the method in Example 1 except that BfaI and TaqI, or MboI and MspI were used as the combination of endonucleases. Similarly, sufficient SNP loci and indel loci can be obtained with a low volume of data, and whether the chromosome of an embryo was abnormal in structure can be determined by constructing a genetic map, so as to distinguish an embryo carrying a balanced translocation or a normal embryo.

Comparative Example 2

In Comparative Example 2, genomic DNA was digested with a combination of NspI and TaqI, and other steps were the same as those in Example 1.

The valid data of chromosomes in Example 1 and Comparative Example 2 was compared. Using 5481105E embryo as an example, the effective loci of the chromosomes are compared in Table 14. Table 14 shows that the data on effective loci (embryo samples) for the combination of endonucleases in Comparative Example 2 is significantly less than that for the combination of endonucleases in Example 1, indicating that the combination of endonucleases in the present disclosure cannot be selected arbitrarily.

TABLE 14

Comparison of effective loci of the chromosomes of embryos in
Example 1 and Comparative Example 2

| Chr | Example 1 | | | | | | Comparative Example 2 | | | | | |
|-----|------|------|------|------|------|------|------|------|------|------|------|------|
|     | Ref | 01E | 02E | 03E | 04E | 05E | Ref | 01E | 02E | 03E | 04E | 05E |
| chr1 | 3401 | 1706 | 2003 | 1130 | 1402 | 1233 | 1393 | 1036 | 601 | 439 | 612 | 943 |
| chr10 | 2298 | 696 | 634 | 1270 | 1170 | 503 | 677 | 388 | 177 | 512 | 330 | 215 |
| chr11 | 2217 | 636 | 767 | 758 | 1123 | 619 | 1280 | 168 | 429 | 436 | 834 | 199 |
| chr12 | 2077 | 882 | 544 | 735 | 777 | 875 | 1084 | 580 | 238 | 215 | 329 | 601 |
| chr13 | 1696 | 839 | 744 | 747 | 519 | 745 | 529 | 390 | 379 | 442 | 378 | 584 |
| chr14 | 1440 | 394 | 400 | 513 | 954 | 737 | 552 | 212 | 97 | 140 | 207 | 421 |
| chr15 | 1322 | 694 | 765 | 783 | 417 | 586 | 690 | 389 | 525 | 606 | 149 | 450 |
| cor16 | 1048 | 576 | 264 | 268 | 384 | 249 | 462 | 221 | 105 | 135 | 134 | 145 |
| chr17 | 1227 | 341 | 377 | 511 | 287 | 600 | 604 | 152 | 161 | 192 | 143 | 413 |
| chr18 | 1274 | 935 | 683 | 603 | 356 | 399 | 299 | 186 | 429 | 406 | 265 | 162 |
| chr19 | 845 | 257 | 183 | 191 | 278 | 494 | 418 | 125 | 79 | 105 | 207 | 301 |
| chr2 | 3884 | 1241 | 1575 | 1778 | 1531 | 1697 | 1502 | 318 | 536 | 512 | 675 | 721 |
| chr20 | 945 | 220 | 241 | 227 | 423 | 544 | 677 | 67 | 128 | 87 | 306 | 389 |
| chr21 | 615 | 118 | 388 | 132 | 166 | 169 | 293 | 77 | 278 | 50 | 149 | 70 |
| chr22 | 487 | 931 | 149 | 240 | 208 | 92 | 235 | 155 | 83 | 139 | 254 | 72 |
| chr3 | 3438 | 948 | 800 | 807 | 1804 | 1710 | 1699 | 411 | 190 | 222 | 539 | 716 |
| chr4 | 3655 | 734 | 1603 | 1870 | 1216 | 1923 | 1432 | 272 | 395 | 909 | 835 | 723 |
| chr5 | 3252 | 1317 | 1570 | 1552 | 666 | 619 | 779 | 571 | 532 | 948 | 449 | 275 |

TABLE 14-continued

Comparison of effective loci of the chromosomes of embryos in
Example 1 and Comparative Example 2

| | Example 1 | | | | | Comparative Example 2 | | | | | |
| Chr | Ref | 01E | 02E | 03E | 04E | 05E | Ref | 01E | 02E | 03E | 04E | 05E |
|---|---|---|---|---|---|---|---|---|---|---|---|---|
| chr6 | 3413 | 1867 | 1838 | 957 | 1569 | 1646 | 1905 | 1144 | 999 | 544 | 724 | 629 |
| chr7 | 2878 | 1631 | 764 | 1569 | 1132 | 909 | 684 | 596 | 164 | 852 | 649 | 205 |
| chr8 | 2073 | 996 | 803 | 916 | 655 | 580 | 721 | 294 | 158 | 267 | 133 | 147 |
| chr9 | 1842 | 512 | 536 | 487 | 601 | 1053 | 552 | 120 | 67 | 79 | 96 | 336 |
| total | 45327 | 17211 | 17632 | 18044 | 17638 | 17982 | 18269 | 7872 | 6752 | 8238 | 8396 | 8719 |

The technical features of the preceding embodiments may be combined in any manner. For brevity of description, all possible combinations of the technical features in the preceding embodiments are not described. However, as long as the combinations of these technical features do not conflict, such combinations are to be construed as being within the scope of the specification.

The preceding embodiments are merely several embodiments of the present disclosure, and the specific and detailed description thereof cannot be construed as limiting the scope of the present disclosure. It is to be noted that those of ordinary skill in the art can make a number of variations and improvements without departing from the concept of the present disclosure, and such variations and improvements are within the scope of the present disclosure. Therefore, the scope of the present disclosure is defined by the appended claims.

What is claimed is:

1. A method for constructing nucleic acid libraries, comprising:

acquiring genomic deoxyribonucleic acid (DNA) of the a target human-derived sample;

cleaving the genomic DNA using a combination of a first endonuclease and a second endonuclease to obtain high-density digestion products; wherein the combination of the first endonuclease and the second endonuclease can produce an average of 2000-5000 cleavage sites per 1 Mb segment in human genome and produce sticky ends of 2-5 nucleotides (nt) at both ends of digestion fragments of the human genome;

ligating the digestion products to sequencing adapters to obtain ligation products; wherein the sequencing adapters comprise a first adapter and a second adapter, the first adapter is capable of being complementary to a sticky end produced after cleavage by the first endonuclease, and the second adapter is capable of being complementary to a sticky end produced after cleavage by the second endonuclease; wherein the first adapter has sequences shown by SEQ ID NO: 1 and SEQ ID NO: 2, and the second adapter has sequences shown by SEQ ID NO: 3 and SEQ ID NO: 4;

screening from the ligation products to obtain fragments of 200 bp to 400 bp;

performing polymerase chain reaction (PCR) amplification using universal primers of high-throughput sequencing platform to obtain sequencing libraries.

2. The method for constructing nucleic acid libraries according to claim 1, wherein the combination of the first endonuclease and the second endonuclease is MboI and NspI, BfaI and TaqI, or MboI and MspI.

3. The method for constructing nucleic acid libraries according to claim 1, wherein the universal primers of the high-throughput sequencing platform comprise a forward primer and a reverse primer, wherein the forward primer complementary pairs with the first adapter, and the reverse primer complementary pairs with the second adapter and has a barcode sequence.

4. The method for constructing nucleic acid libraries according to claim 3, wherein the forward primer has a sequence shown by SEQ ID NO: 5 and the reverse primer has a sequence shown by SEQ ID NO: 6.

5. The method for constructing nucleic acid libraries according to claim 1, wherein in the cleavage step, the first endonuclease and the second endonuclease have a volume ratio of 1:(0.8-1.2).

6. The method for constructing nucleic acid libraries according to claim 1, wherein the ligation products are screened through magnetic bead sorting to obtain the fragments of 200 bp to 400 bp.

7. The method for constructing nucleic acid libraries according to claim 1, wherein the step of acquiring the genomic DNA comprises: acquiring cells from an embryo developed to a cleavage stage or a blastocyst stage and performing whole genome amplification of DNA in these cells.

8. The method for constructing nucleic acid libraries according to claim 1, further comprising: determining concentration of the sequencing libraries.

9. A method for analyzing chromosomal structural rearrangements of preimplantation embryos based on reduced-representation genome sequencing, comprising: constructing sequencing libraries of an embryo sample and at least one parent of the embryo sample by the method for constructing nucleic acid libraries according to claim 1, then performing sequencing, and analyzing chromosomes of the embryo sample according to a sequencing result.

10. The method for analyzing chromosomal structural rearrangements of preimplantation embryos according to claim 9, wherein the analysis step comprises: analyzing chromosomal structural rearrangements and analyzing chromosomal aneuploidy.

* * * * *